United States Patent
Okubo et al.

(10) Patent No.: US 6,559,276 B2
(45) Date of Patent: May 6, 2003

(54) ASYMMETRIC DISULFIDE COMPOUNDS, METHOD FOR PRODUCING THE SAME, AND OPTICAL PRODUCTS

(75) Inventors: Tsuyoshi Okubo, Tokyo (JP); Jian Jiang, Tokyo (JP)

(73) Assignee: Hoya Corporation, Tokyo (JP)

( * ) Notice: Subject to any disclaimer, the term of this patent is extended or adjusted under 35 U.S.C. 154(b) by 29 days.

(21) Appl. No.: 09/984,070

(22) Filed: Oct. 26, 2001

(65) Prior Publication Data

US 2002/0099167 A1 Jul. 25, 2002

(30) Foreign Application Priority Data

Oct. 26, 2000 (JP) ........................................ 2000-327112
Oct. 26, 2000 (JP) ........................................ 2000-327113

(51) Int. Cl.$^7$ .............................................. C08G 75/04
(52) U.S. Cl. ........................ 528/374; 528/375; 528/373
(58) Field of Search ................................. 528/374, 375, 528/373; 351/159

(56) References Cited

FOREIGN PATENT DOCUMENTS

| JP | 58-164615 | 9/1983 |
|---|---|---|
| JP | 60-199016 | 10/1985 |
| JP | 02-270859 | 11/1990 |
| JP | 03-236386 | 10/1991 |
| JP | 05-148340 | 6/1993 |
| JP | 07-118390 | 5/1995 |
| JP | 09-071580 | 3/1997 |
| JP | 09-110979 | 4/1997 |

*Primary Examiner*—Duc Truong
(74) *Attorney, Agent, or Firm*—Finnegan, Henderson, Farabow, Garrett & Dunner, L.L.P.

(57) ABSTRACT

Asymmetric disulfide compounds and methods for their preparation are described. An optical product can be made of a polymer that is obtained by using at least one asymmetric disulfide compound as an essential monomer component. These polymers can be used to form an optical product having a high refractive index and a high Abbe's number and having superior heat resistance, superior weather resistance and superior transparency.

25 Claims, No Drawings

ASYMMETRIC DISULFIDE COMPOUNDS, METHOD FOR PRODUCING THE SAME, AND OPTICAL PRODUCTS

The present invention relates to an optical product such as plastic lenses, prisms, optical fibers, substrates for information recording, IR-absorbing filters, color filters and others. These optical products are made from a polymer obtained by using an asymmetric disulfide compound as an essential monomer component.

The present invention also relates to novel asymmetric disulfide compounds and to a method for producing the same. The novel asymmetric disulfide compounds are useful as a starting material for optical materials having a high refractive index and a high Abbe's number.

BACKGROUND OF THE INVENTION

Plastics are used for various optical applications these days, for example, for lenses and others, as being lightweight, hardly broken and easily colored when compared with glass. For optical plastic materials, generally used are poly(diethylene glycol bisallyl carbonate) (CR-39) and poly(methyl methacrylate). However, these plastics have a refractive index of at most 1.50. Therefore, for example, when they are used for lens materials, the lenses produced become thicker with the increase in their power, and they lose the advantage of plastics that are lightweight. In particular, powerful concave lenses are thick at their periphery, and are therefore unfavorable as causing birefringence and chromatic aberration. For spectacles, in addition, such thick lenses are often not aesthetic. For obtaining thin lenses, it is effective to increase the refractive index of the materials for them. In general, the Abbe's number of glass and plastics decreases with the increase in their refractive index, and, as a result, their chromatic aberration increases. Accordingly, desired are plastic materials having a high refractive index and a high Abbe's number.

For plastic materials having such properties, for example, (1) polyurethanes obtained through addition-polymerization of a polyol having bromine in the molecule and a polyisocyanate (Japanese Patent Laid-Open No. 164615/1983); and (2) polythiourethanes obtained through addition-polymerization of a polythiol and a polyisocyanate (Japanese Patent Publication Nos. 58489/1992 and 148340/1993), are proposed. For the starting material, polythiol for the polythiourethanes of above (2), specifically proposed are branched polythiols having an increased sulfur atom content (Japanese Patent Laid-Open Nos. 270859/1990 and 148340/1993), and polythiols into which is introduced a dithian structure for increasing their sulfur atom content (Japanese Patent Publication No. 5323/1994 and Japanese Patent Laid-Open No. 118390/1995). Further proposed are (3) polymers of an alkyl sulfide having a polymerization-functional group, episulfide (Japanese Patent Laid-Open Nos. 71580/1997 and 110979/1997).

However, though their refractive index is increased a little, the polyurethanes of above (1) still have a low Abbe's number and have some other drawbacks in that their light fastness is poor, their specific gravity is high and therefore they are not lightweight. Of the polythiourethanes (2), those for which the starting polythiol used has a high sulfur content have an increased refractive index ranging from approximately 1.60 to 1.68, but their Abbe's number is lower than that of optical inorganic glass having a refractive index on the same level. Therefore, they still have a problem in that their Abbe's number must be increased more. On the other hand, one example of the alkyl sulfide polymers (3) having an Abbe's number of 36 has an increased refractive index of 1.70. The lenses made of such polymer can be made extremely thin and lightweight. However, still desired are plastic materials of which both the Abbe's number and the refractive index are more increased.

BRIEF SUMMARY OF THE INVENTION

The present invention provides an optical product made of optical material having a high refractive index and a high Abbe's number and having superior heat resistance, superior weather resistance and superior transparency. The invention also provides novel asymmetric disulfide compounds capable of giving optical materials of which both the refractive index and the Abbe's number are high and which have superior heat resistance, superior weather resistance and superior transparency, and provides an efficient method for producing the compounds.

DETAILED DESCRIPTION OF THE INVENTION

The invention provides an optical product comprising a polymer obtained by using at least one asymmetric disulfide compound as an essential monomer component. Preferably, the asymmetric disulfide compound is one obtained through reaction of (A) an O-alkyl-S-substituted sulfenylthiocarbonate with (B) a thiol.

The component (A), O-alkyl-S-substituted sulfenylthiocarbonate may be one obtained through reaction of an alkoxycarbonylsulfenyl halide (for example, a chloride) with a thiol that differs from the thiol for the component (B) Preferred examples of the substituent for the S-substitution in the compound are hydrocarbon groups, including, for example, an alkyl group, an alkenyl group (a vinyl group, etc.), an alkynyl group (a propargyl group, etc.), etc.

The asymmetric disulfide compound may be produced via the O-alkyl-S-substituted sulfenylthiocarbonate through reaction of an alkoxycarbonylsulfenyl halide with two different types of thiols, as in the following reaction schemes (1) and (2).

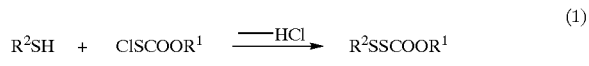

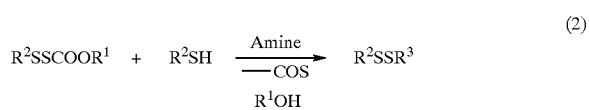

In the above schemes, $R^1$ represents an alkyl group (e.g., a lower alkyl group, preferably a methyl group, an ethyl group, etc.); $R^2$ represents a thiol residue; and $R^3$ represents a thiol residue that differs from $R^2$.

For the two different types of thiols, various thiols can be used. For example, when the thiol used for synthesizing the component (A) is 1,2-dimercaptoethane, 1,2,3-trimercaptopropane, trimercaptomethane or dimercaptomethane, the thiol of the component (B) is preferably 2,3-epithiopropylmercaptan; and when the thiol used for synthesizing the component (A) is vinylmercaptan, propargylmercaptan or 2,3-epithiopropylmercaptan, the thiol of the component (B) is preferably 1,2-dimercaptoethane, 1,2,3-trimercaptopropane, trimercaptomethane or dimercaptomethane.

The reaction in the reaction scheme (1) is carried out in a solvent (e.g., dichloromethane) at 0 to −78° C. for 1 to 12 hours with dehydrochlorination. The resulting O-alkyl-S-substituted sulfenylthiocarbonate is, after optionally isolated and purified, then mixed with a pure thiol in the presence of from $10^{-6}$ to $10^{-3}$ mol % of an amine catalyst with stirring, according to the reaction scheme (2), to obtain the intended asymmetric disulfide of the invention.

The production method may be described as follows. Specifically, even though the thiol $R^2SH$ to constitute a part of the asymmetric disulfide compound is unstable at ambient temperature under atmospheric pressure, it is reacted with an alkoxycarbonylsulfenyl halide to give a stable O-alkyl-S-substituted sulfenylthiocarbonate having the structure of the thiol $R^2SH$ introduced thereinto, which can be stored at ambient temperature under atmospheric pressure. The reaction goes well even at relatively low temperatures at which the thiol is stable.

In addition, the reaction of the O-alkyl-S-substituted sulfenylthiocarbonate with the other thiol $R^3SH$ (the reaction according to the reaction scheme (2)) goes quantitatively, and gives the intended asymmetric disulfide that is substantially colorless and pure. The by-products, carbonyl sulfide and alkyl alcohol $R^1OH$, are both volatile, and can be readily removed under reduced pressure.

Accordingly, an asymmetric disulfide not requiring purification is obtained from the pure O-alkyl-S-substituted sulfenylthiocarbonate and a thiol. In case where the intended asymmetric disulfide is difficult to purify or where less colored optical materials are desired to be obtained, this production method is useful.

In the alkoxycarbonylsulfenyl halide to be used in the first reaction, the alkoxy group is preferably a methoxy group or an ethoxy group for enabling easy removal of the alcohol to be formed in the next reaction.

The amine catalyst that may be used in the reaction scheme (2) includes triethylamine, benzylamine, dicyclohexylmethylamine, dimethylcyclohexylamine, 2,4,6-tris(dimethylaminomethyl)phenol, etc.

The asymmetric disulfide compounds obtained in the method described above are useful as a starting material for optical materials. One or more of the asymmetric disulfide compounds may be used either singly or in combination, and formed into polymers for optical materials. If desired, optional components of, for example, episulfide compounds, epoxy compounds, mixtures of iso(thio)cyanates and thiols to form thiourethanes, thiols, homopolymerizable vinyl monomers, etc. may be added to the asymmetric disulfide compounds for suitably improving the physical properties of the polymers produced from them.

Examples of the optional episulfide compounds are linear organic compounds such as bis(β-epithiopropylthio)methane, 1,2-bis(β-epithiopropylthio)ethane, 1,3-bis(β-epithio-propylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)-thio]ethane, 1-(β-epithiopropylthio)-2-[(2-(2-β-epithiopropylhioethyl)thioethyl)thio]ethane, etc.; branched organic compounds such as tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(βepithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthio methyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropyl-thio)-4,7-bis(β-epithiopropylthiomethyl)-3,6,9-trithiaundecane, etc., and compounds derived from them by substituting at least one hydrogen of the episulfide group therein with a methyl group; alicyclic organic compounds such as 1,3- and 1,4-bis(β-epithiopropylthio)cyclohexanes, 1,3- and 1,4-bis(β-epithiopropylthiomethyl)cyclohexanes, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithian, 2,5-bis(β-epithiopropylthioethylthiomethyl)-1,4-dithian, etc., and compounds derived from them by substituting at least one hydrogen of the episulfide group therein with a methyl group; and aromatic organic compounds such as 1,3- and 1,4-bis(β-epithiopropylthio)benzenes, 1,3- and 1,4-bis(β-epithiopropylthiomethyl)benzenes, bis[4-(β-epithiopropylthio)phenyl]methane, 2,2-bis[4-(β-epithiopropylthio)phenyl]propane, bis[4-(β-epithiopropylthio)-phenyl]sulfide, bis[4-(β-epithiopropylthio)phenyl]sulfone, 4,4'-bis(β-epithiopropylthio)biphenyl, etc., and compounds derived from them by substituting at least one hydrogen of the episulfide group therein with a methyl group, etc. One or more of these may be used herein either singly or as combined. Their amount to be used preferably is from 0.01 to 50 mol % of the total amount of the essential component, asymmetric disulfide.

Examples of the optional epoxy compounds are phenolic epoxy compounds produced through condensation of polyphenol compounds, such as hydroquinone, catechol, resorcinol, bisphenol A, bisphenol F, bisphenol sulfone, bisphenol ether, bisphenol sulfide, bisphenol sulfide, bisphenol A halides, novolak resins, etc., with epihalohydrins; alcoholic epoxy compounds produced through condensation of polyalcohol compounds, such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerin, trimethylolpropane trimethacrylate, pentaerythritol, 1,3- and 1,4-cyclohexanediols, 1,3- and 1,4-cyclohexanedimethanols, hydrogenated bisphenol A, bisphenol A-ethylene oxide adduct, bisphenol A-propylene oxide adduct, etc., with epihalohydrins; glycidyl ester-based epoxy compounds produced through condensation of polycarboxylic acid compounds, such as adipic acid, sebacic acid, dodecanedicarboxylic acid, dimer acids, phthalic acid, iso-and terephthalic acids, tetrahydrophthalic acid, methyltetrahydrophthalic acid, hexahydrophthalic acid, hexahydroisophtalic acid, hexahydroterephthalic acid, HET acid, nadic acid, maleic acid, succinic acid, fumaric acid, trimellitic acid, benzenetetracarboxylic acid, benzophenonetetracarboxylic acid, naphthalenedicarboxylic acid, diphenyldicarboxylic acid, etc., with epihalohydrins; amine-based epoxy compounds produced through condensation of primary amines, such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl) ether, 1,2-bis(3-aminopropoxy)ethane, 1,3-bis(3-amino-propoxy)-2,2'-dimethylpropane, 1,2-, 1,3- or 1,4-bisaminocyclohexane, 1,3- or 1,4-bisaminomethylcyclohexane, 1,3-or 1,4-bisaminoethylcyclohexane, 1,3- or 1,4-bisaminopropylcyclohexane, hydrogenated 4,4'-diaminodiphenylmethane, isophoronediamine, 1,4-bisaminopropylpiperazine, m- or p-phenylenediamine, 2,4- or 2,6-tolylenediamine, m- or p-xylylenediamine, 1,5- or 2,6-naphthalenediamine, 4,4'-diaminodiphenylmethane, 4,4'-diaminodiphenyl ether, 2,2-(4,4'-diaminodiphenyl) propane, etc., or secondary amines, such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,3-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5- or 2,6-dimethylpiperazine, homo-piperazine, 1,1-di(4-piperidyl) methane, 1,2-di(4-piperidyl)ethane, 1,3-di(4-piperidyl) propane, 1,4-di(4-piperidyl)butane, etc., with epihalohydrins; alicyclic epoxy compounds such as 3,4-epoxycyclohexyl 3,4-epoxycyclohexanecarboxylate, vinylcyclohexane dioxide, 2-(3,4-epoxycyclohexyl)-5,5-spiro-3, 4-epoxycyclohexane-meta dioxane, bis(3,4-epoxycyclohexyl) adipate, etc.; epoxy compounds produced through epoxydation of unsaturated compounds, such as cyclopentadiene epoxide, epoxidated soybean oil, epoxydated polybutadiene, vinylcyclohexane epoxide, etc.; urethane-based epoxy compounds obtained from the above-mentioned polyalcohols, phenolic compounds with diisocyanates and glycidols, etc. One or more of these may be used herein either singly or as combined. Their amount to be used preferably is from 0.01 to 50 mol % of the total amount of the asymmetric disulfide compound of the invention.

Examples of the optional iso(thio)cyanates are xylylene diiso(thio)cyanate, 3,3'-dichlorodiphenyl 4,4'-diiso(thio) cyanate, 4,4'-diphenylmethane diiso(thio)cyanate, hexamethylene diiso(thio)cyanate, 2,2',5,5'-tetrachlorodiphenyl 4,4'-diiso(thio)cyanate, tolylene diiso(thio)cyanate, bis(iso (thio)cyanatomethyl)cyclohexane, bis(4-iso(thio)-cyanatocyclohexyl)methane, bis(4-iso(thio) cyanatomethylcyclohexyl)methane, cyclohexane diiso(thio) cyanate, isophorone diiso(thio)cyanate, 2,5-bis(iso(thio) cyanatomethyl)bicyclo[2,2,2]octane, 2,5-bis(iso(thio) cyanatomethyl)bicyclo[2,2,1]heptane, 2-iso(thio) cyanatomethyl-3-(3-iso(thio)cyanatopropyl)-5-iso(thio) cyanatomethyl-bicyclo[2,2,1]heptane, 2-iso(thio) cyanatomethyl-3-(3-iso(thio)-cyanatopropyl)-6-iso(thio) cyanatomethyl-bicyclo-[2,2,1]heptane, 2-iso(thio) cyanatomethyl-2-[3-iso(thio)-cyanatopropyl]-5-iso(thio) cyanatomethyl-bicyclo[2,2,1]-heptane, 2-iso(thio) cyanatomethyl-2-(3-iso(thio)cyanatopropyl)-6-iso(thio) cyanatomethyl-bicyclo[2,2,1]heptane, 2-iso(thio) cyanatomethyl-3-(3-iso(thio)cyanatopropyl)-6-(2-iso(thio) cyanatoethyl)-bicyclo[2,2,1]heptane 2-iso(thio)-cyanatomethyl-3-(3-iso(thio)cyanatopropyl)-6-(2-iso(thio)-cyanatoethyl)-bicyclo[2,2,1]hepta 2-iso(thio) cyanatomethyl-2-(3-iso(thio)cyanatopropyl)-5-(2-iso(thio) cyanatoethyl)-bicyclo[2,2,1]heptane 2-iso(thio) cyanatomethyl-2-(3-iso(thio)cyanatopropyl)-6-(2-iso(thio) cyanatoethyl)-bicyclo[2,2,1]heptane Examples of the optional thiols are 1,2-ethanedithiol, 1,3-propanedithiol, tetrakismercaptomethylmethane, pentaerythritol tetrakismercaptopropionate, pentaerythritol tetrakismercaptoacetate, 2,3-dimercaptopropanol, dimercaptomethane, trimercaptomethane, 1,2-benzenedithiol, 1,3-benzenedithiol, 2,5-bis (mercaptomethyl)-1,4-dithian, 1,4-benzenedithiol, 1,3,5-benzenetrithiol, 1,2-dimercaptomethylbenzene, 1,3-dimercaptomethylbenzene, 1,4-dimercaptomethylbenzene, 1,3,5-trimercaptomethylbenzene, toluene-3,4-dithiol, 1,2,3-trimercaptopropane, 1,2,3,4-tetramercaptobutane, etc.

Examples of the optional, homopolymerizable vinyl monomers are compounds having an ester structure of acrylic or methacrylic acid with mono- or polyalcohol, such as methyl acrylate, methyl methacrylate, ethyl acrylate, ethyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, polyethylene glycol diacrylate, polyethylene glycol dimethacrylate, 1,3-butylene glycol diacrylate, 1,3-butylene glycol dimethacrylate, 1,6-hexanediol diacrylate, 1,6-hexanediol dimethacrylate, neopentyl glycol diacrylate, neopentyl glycol dimethacrylate, polypropylene glycol diacrylate, polypropylene glycol dimethacrylate, 2,2-bis[4-(acryloxyethoxy)phenyl]propane, 2,2-bis[4-(methacryloxyethoxy)phenyl]propane, 2,2-bis[4-(acryloxydiethoxy)phenyl]propane, 2,2-bis[4-(methacryloxydiethoxy)phenyl]propane, 2,2-bis[4-(acryloxypolyethoxy)phenyl]propane, 2,2-bis[4-(methacryloxypolyethoxy)phenyl]propane, trimethylolpropane triacrylate, trimethylolpropane trimethacrylate, pentaerythritol tetraacrylate, pentaerythritol tetramethacrylate, bis(2,2,2-trimethylolethyl) ether hexaacrylate, bis(2,2,2-trimethylolethyl) ether hexamethacrylate, etc.; allyl compounds such as allyl sulfide, diallyl phthalate, diethylene glycol bisallyl carbonate, etc.; and vinyl compounds such as acrolein, acrylonitrile, vinyl sulfide, etc.; aromatic vinyl compounds such as styrene, (α-methylstyrene, methylvinylbenzene, ethylvinylbenzene, α-chlorostyrene, chlorovinylbenzene, vinylbenzyl chloride, paradivinylbenzene, metadivinylbenzene, etc. One or more of these may be used herein either singly or as combined.

The amount of optical iso (thio) cyanates, thiols or homopolymerizable vinyl monomers to be used preferably is from 0.01 to 20 mol % of the total amount of the asymmetric disulfide compound of the invention.

To the polymerizable composition containing the asymmetric disulfide compound of the invention, if desired, optionally added is any other additives, such as UV absorbent, antioxidant, discoloration inhibitor, fluorescent dye and the like for improving the weather resistance of the resulting polymers, not interfering with the object of the invention. Also if desired, catalysts may be used for improving the polymerization reaction of the compound. For the catalysts usable herein, for example, amines, phosphines, quaternary ammonium salts, quaternary phosphonium salts, tertiary sulfonium salts, secondary iodonium salts, mineral acids, Lewis acids, organic acids, silicic acids, tetrafluoroboric acid and the like are effective in polymerization of episulfides and epoxy compounds; radical generators such as azobisisobutyronitrile, azobisdimethylvaleronitrile, benzoyl peroxide and the like are effective in polymerization of vinyl compounds; and dimethyltin dichloride, dilauryltin dichloride, amines and the like are effective in polymerization of iso(thio)cyanates with thiols.

Using the asymmetric disulfide compounds of the invention, optical materials can be produced, for example, according to the method described below.

A uniform composition containing the above-mentioned polymerizable compounds and other optional additives is first prepared, and this is cast into a glass or metal mold combined with a resin-made gasket, and heated and cured therein, according to a known method of casting polymerization. If desired, the mold may be pretreated for lubrication or a lubricant may be added to the composition, for facilitating good release of the resin after molding. The polymerization temperature varies, depending on the compounds used, but may generally be from −20° C. to +150° C.; and the polymerization time may be from about 0.5 to 72 hours. After having been thus polymerized and released from the mold, the cast moldings may be readily dyed with any ordinary disperse dye in water or in an organic solvent. For facilitating the dyeing, a carrier may be added to the dye dispersion, or the dyeing bath may be heated. Though not limited thereto, the thus-obtained optical materials are especially useful for optical products such as plastic lenses, etc.

EXAMPLES

The invention is described more concretely with reference to the following Examples, which, however, are not intended to restrict the scope of the invention. The physical properties of the asymmetric disulfide compounds obtained in the Examples, and those of the polymers obtained in the following Application Examples and Comparative Application Examples were measured according to the methods described below.

<1> Physical properties of asymmetric disulfide compounds:
The refractive index ($n_D$) and the Abbe's number ($v_D$) of the compounds were measured at 25° C. with a precision refractometer, Kalnew's KPR-200.

<2> Physical properties of polymers:
(a) Refractive index ($n_D$) and Abbe's number ($v_D$):
Measured in the same manner as above.
(b) Appearance: Visually checked.
(c) Weather resistance:
The plastic lens to be tested was set in a weatherometer equipped with a sunshine carbon arc lamp. After having been exposed to the light from the lamp for 200 hours, it was taken out, and its color was compared with the hue of the plastic lens before the test.
The evaluation was made according to the following criteria.

| o: | No change. |
| Δ: | Yellowed but a little. |
| x: | Yellowed. |

(d) Heat resistance:
Measured with a TMA analyzer made by Rigaku Co., Ltd. Concretely, using a pin having a diameter of 0.5 mm, TMA of each sample was measured under a load of 98 mN (10 gf) at a heating rate of 10° C./min. From the peak temperature appearing in the chart, the heat resistance of the sample was evaluated.

Reference Example 1

Production example of 1,6-bis(2,3-epithiopropyl)-1,2,5,6-tetrathiahexane

A solution of 1,2-dimercaptoethane (5.31 g) in dichloromethane (28 ml) was added dropwise to a solution of methoxycarbonylsulfenyl chloride (14.27 g) in dichloromethane (50 ml) over a period of 1 hour at 0° C., and the resulting mixture was stirred at room temperature for 2 hours. The reaction mixture was washed with water until it had become neutral, and the solvent was evaporated away. The crystal thus obtained was recrystallized from ethanol to obtain an S-substituted sulfenyl O-methoxythiocarbonate derivative (13.76 g). To a solution of this compound (10.52 g) in dichloromethane (35 ml), added were 2,3-epithiopropylmercaptan (8.15 g) and triethylamine (21 μl). This was stirred at room temperature for 3 hours, with removing carbonyl sulfide and methanol under reduced pressure, and the intended product (13.01 g) was obtained.

The refractive index ($n_D$) of the compound was 1.666; and the Abbe's number ($v_D$) thereof was 30.9. The compound was analyzed to determine its structure. Its data are as follows:

$^1$H-NMR (solvent CDCl$_3$; internal standard substance TMS): δ2.51 (dd, 4H), δ2.72 (m, 2H), δ3.05 (s, 4H), δ3.19 (m, 4H).

Reference Example 2

Production example of 1,5-bis(2,3-epithiopropyl)-1,2,4,5-tetrathiapentane

A solution of dimercaptomethane (3.52 g) in dichloromethane (22 ml) was added dropwise to a solution of methoxycarbonylsulfenyl chloride (11.12 g) in dichloromethane (43.9 ml) over a period of 1 hour at 0° C., and the resulting mixture was stirred at 0° C. for 3 hours. The reaction mixture was washed with water until it had become neutral, and the solvent was evaporated away. The resulting residue was distilled under 1.07 Pa to obtain a fraction at 115 to 117° C., S-substituted sulfenyl O-methoxythiocarbonate derivative (6.83 g). To the compound (4.52 g), added were 2,3-epithiopropylmercaptan (3.69 g) and 2,4,6-tris (dimethylaminomethyl)phenol (1.8 mg). This was stirred at room temperature for 3 hours, with removing carbonyl sulfide and methanol under reduced pressure, and the intended product (4.53 g) was obtained.

The refractive index ($n_D$) of the compound was 1.681; and the Abbe's number ($v_D$) thereof was 29.7. The compound was analyzed to determine its structure. Its data are as follows:

1H-NMR (solvent CDCl$_3$; internal standard substance TMS): δ2.51 (dd, 4H), δ2.85 (m, 2H), δ3.23 (s, 4H), δ4.09 (m, 2H).

Reference Example 3

Production example of 1,7-divinyl-4-(1,2-dithia-3-butenyl)-1,2,6,7-tetrathiaheptane A solution of vinylmercaptan (5.88 g) in dichloromethane (48.9 ml) was added dropwise to a solution of methoxycarbonylsulfenyl chloride (12.38 g) in dichloromethane (48.9 ml) over a period of 1 hour at −30° C., and the resulting mixture was stirred at −12° C. for 6 hours. The reaction mixture was warmed up to room temperature, and then washed with water until it had become neutral, and the solvent was evaporated away. The resulting residue was distilled under 267 Pa to obtain a fraction at 64° C., S-substituted sulfenyl O-methoxythiocarbonate derivative (12.63 g). To the compound (3.92 g), added were 1,2,3-trimercaptopropane (1.22 g) and 2,4,6-tris(dimethylaminomethyl)phenol (1.4 mg). This was stirred at room temperature for 3 hours, with removing carbonyl sulfide and methanol under reduced pressure, and the intended product (2.63 g) was obtained.

The refractive index ($n_D$) of the compound was 1.646; and the Abbe's number ($\nu_D$) thereof was 34.5. The compound was analyzed to determine its structure. Its data are as follows:

$^1$H-NMR (solvent CDCl$_3$; internal standard substance TMS): δ3.19 (m, 6H), δ3.45 (m, 1H), δ5.67 (dd, 6H), δ6.44 (dd, 3H).

Example 1

Production of optical material made of polymer 0.05 mols of 1,6-bis(2,3-epithiopropyl)-1,2,5,6-tetrathiahexane obtained in Example 1 and $2 \times 10^{-5}$ mols of a polymerization catalyst, tetra(n-butyl)phosphonium bromide were mixed to form a uniform mixture, and this was cast into a glass mold for producing two lenses. In the mold, this was polymerized under heat at 50° C. for 10 hours, then at 60° C. for 5 hours and then at 120° C. for 3 hours to obtain a polymer in a lens shape. The physical properties of the thus-obtained polymer are given in Table 2. As in Table 2, the polymer obtained in this Application Example 1 was colorless and transparent. The refractive index ($n_D$) was 1.735 and was extremely high; the Abbe's number ($\nu_D$) was 32.1 and was also high (i.e., of low dispersion); and the weather resistance and heat resistance (117° C.) were both good. Accordingly, the polymer obtained herein was favorable to optical materials.

Examples 2 to 5

Production of optical material made of polymer

Polymers in a lens shape were produced in the same manner as in Example 1, for which, however, used were the asymmetric disulfide compound of the invention, episulfide compound, vinyl monomer and polymerization catalyst as in Table 1, and the polymerization condition was suitably varied. Their physical properties are given in Table 2. As in Table 2, these polymers obtained in Application Examples 2 to 5 were also colorless and transparent. Their refractive index ($n_D$) was from 1.728 to 1.776 and was extremely high; their Abbe's number ($\nu_D$) was from 30.3 to 34.6 and was also high (i.e., of low dispersion); and their weather resistance and heat resistance (117 to 132° C.) were both good.

Comparative Example 1

As in Table 1, 0.1 mol of pentaerythritol tetrakismercaptopropionate, 0.2 mols of m-xylylene diisocyanate and $1.0 \times 10^{-4}$ mols of dibutyltin dichloride were mixed to form a uniform mixture, and this was cast into a glass mold for producing two lenses. In the mold, this was polymerized under heat at 50° C. for 10 hours, then at 60° C. for 5 hours and then at 120° C. for 3 hours to obtain a polymer in a lens shape. The physical properties of the thus-obtained polymer lenses are given in Table 2. As in Table 2, the polymer obtained in this Comparative Example 1 was colorless and transparent, but the $n_D/\nu_D$ was 1.59/36, or that is, the refractive index was low. In addition, the heat resistance (86° C.) was not good.

Comparative Examples 2 and 3

Polymers in a lens shape were produced in the same manner as in Comparative Example 1, for which, however, used were the materials as in Table 1. Their physical properties are given in Table 1. As in Table 2, the polymers of Comparative Example 2 had $n_D/\nu_D$ of 1.67/28, or that is the $n_D$ and $\nu_D$ were both low. Though their heat resistance (94° C.) was relatively good, their weather resistance was not good, and, in addition, they were yellowed. The polymer of Comparative Example 3 had a relatively high $\nu_D$ of 36, it had good weather resistance, and it was colorless and transparent. However, the heat resistance (90° C.) was not good, the $n_D$ was 1.70 and was not so high, and it was brittle.

The abbreviations in Table 1 are described below.

M1: 1,6-Bis(2,3-epithiopropyl)-1,2,5,6-tetrathiahexane
M2: 1,2,3-Tris(4,5-epithio-1,2-dithiapentyl)propane
M3: 2,3-epithiopropyl sulfide
M4: 1,5-Bis(2,3-epithiopropyl)-1,2,4,5-tetrathiapentane
M5: 2,5-Bis(mercaptomethyl)-1,4-dithian
M6: 2,5-Bis(isocyanatomethyl)-1,4-dithian
M7: 1,7-Divinyl-4-(1,2-dithia-3-butenyl)-1,2,6,7-tetrathiaheptane
M8: Dimercaptomethane
M9: 2,5-Bis(vinylthiomethyl)-1,4-dithian
RM1: Pentaerythritol tetrakis(mercaptopropionate)
RM2: m-Xylylene diisocyanate
RM3: 1,3,5-Trimercaptobenzene
CT1: Tetra(n-butyl)phosphonium bromide
CT2: Triethanolamine
CT3: Dibutyltin dichloride
CT4: Azobis(dimethylvaleronitrile)

TABLE 1

|  | Starting monomer(s) (mol) | Polymerization catalyst (mol) |
| --- | --- | --- |
| Example 1 | M1 (0.05) | CT1 ($2 \times 10^{-5}$) |
| Example 2 | M2/M3 (0.045/0.005) | CT1 ($2 \times 10^{-5}$) |
| Example 3 | M4 (0.05) | CT2 ($2 \times 10^{-5}$) |
| Example 4 | M3/M4/M5/M6 (0.002/0.04/0.004/0.004) | CT1/CT3 ($1.7 \times 10^{-5}$/$4 \times 10^{-6}$) |
| Example 5 | M7/M8/M9 (0.038/0.061/0.005) | CT4 ($3.7 \times 10^{-4}$) |
| Comparative Example 1 | RM1/RM2 (0.1/0.2) | CT3 ($1.0 \times 10^{-4}$) |
| Comparative Example 2 | RM3/RM2 (0.2/0.3) | CT3 ($1.5 \times 10^{-4}$) |
| Comparative Example 3 | M3 (0.1) | CT1 ($1.0 \times 10^{-4}$) |

TABLE 2

| | $n_D/v_D$ | Appearance | Heat resistance (° C.) | Weather resistance |
|---|---|---|---|---|
| Example 1 | 1.735/32.1 | colorless and transparent, hard | 117 | ○ |
| Example 2 | 1.728/34.6 | colorless and transparent, hard | 121 | ○ |
| Example 3 | 1.762/30.8 | Colorless and transparent, hard | 124 | ○ |
| Example 4 | 1.751/31.2 | Colorless an transparent, hard | 118 | ○ |
| Example 5 | 1.776/30.3 | Colorless and transparent, hard | 132 | ○ |
| Comparative Example 1 | 1.59/36 | Colorless and transparent, hard | 86 | ○ |
| Comparative Example 2 | 1.67/28 | Pale yellow and transparent, hard | 94 | x |
| Comparative Example 3 | 1.70/36 | Colorless and transparent, brittle | 90 | ○ |

The asymmetric disulfide compounds of the invention have a high sulfur content and are useful as starting compounds for optical materials. The optical product of the invention obtained by using at least one asymmetric disulfide compound as an essential monomer component, has a high refractive index and a high Abbe's number, and has superior heat resistance, superior weather resistance and superior transparency. Therefore, it is suitable, for example, for lenses such as those for spectacles and cameras, and also for prisms, optical fibers, substrates for recording media such as optical discs and magnetic discs, as well as for color filters, IR-absorbing filters, etc.

What is claimed is:

1. An asymmetric disulfide compound obtained through reaction of a component (A) O-alkyl-S-substituted sulfenylthiocarbonate with a component (B) thiol.

2. The asymmetric disulfide compound as claimed in claim 1, wherein the component (A) O-alkyl-S-substituted sulfenylthiocarbonate is obtained through reaction of an alkoxycarbonylsulfenyl halide with a thiol.

3. The asymmetric disulfide compound as claimed in claim 2, wherein the component (B) thiol is 2,3-epithiopropylmercaptan, and the thiol used for synthesizing the component (A) is 1,2-dimercaptoethane, 1,2,3-trimercaptopropane, trimercaptomethane or dimercaptomethane.

4. The asymmetric disulfide compound as claimed in claim 2, wherein the component (B) thiol is 1,2-dimercaptoethane, 1,2,3-trimercaptopropane, trimercaptomethane or dimercaptomethane, and the thiol used for synthesizing the component (A) is vinylmercaptan, propargylmercaptan or 2,3-epithiopropylmercaptan.

5. An asymmetric disulfide compound selected from 1,6-bis(2,3-epithiopropyl)-1,2,5,6-tetrathiahexane, 1,5-bis(2,3-epithiopropyl)-1,2,4,5-tetrathiapentane and 1,7-divinyl-4-(1,2-dithia-3-butenyl)-1,2,6,7-tetrathiaheptane.

6. A method for producing an asymmetric disulfide comprising reacting an alkoxycarbonylsulfenyl halide with a thiol, followed by reacting the resulting O-alkyl-S-substituted sulfenylthiocarbonate with a thiol that differs from the thiol used in the previous reaction.

7. A method for producing an asymmetric disulfide, comprising reacting a component (A) O-alkyl-S-substituted sulfenylthiocarbonate with a component (B) thiol.

8. The method for producing an asymmetric disulfide as claimed in claim 7, wherein the component (A) O-alkyl-S-substituted sulfenylthiocarbonate is one obtained through reaction of an alkoxycarbonylsulfenyl halide with a thiol.

9. The method for producing an asymmetric disulfide as claimed in claim 8, wherein the component (B) thiol is 2,3-epithiopropylmercaptan, and the thiol used for synthesizing the component (A) is 1,2-dimercaptoethane, 1,2,3-trimercaptopropane, trimercaptomethane or dimercaptomethane.

10. The method for producing an asymmetric disulfide as claimed in claim 8, wherein the component (B) thiol is 1,2-dimercaptoethane, 1,2,3-trimercaptopropane, trimercaptomethane or dimercaptomethane, and the thiol used for synthesizing the component (A) is vinylmercaptan, propargylmercaptan or 2,3-epithiopropylmercaptan.

11. An optical product comprising a polymer obtained by using at least one asymmetric disulfide compound as an essential monomer component.

12. The optical product as claimed in claim 11, wherein the asymmetric disulfide compound is one obtained through reaction of (A) an O-alkyl-S-substituted sulfenylthiocarbonate with (B) a thiol.

13. The optical product as claimed in claim 11, wherein the asymmetric disulfide compound is one obtained by reacting an alkoxycarbonylsulfenyl halide with a thiol followed by reacting the resulting O-alkyl-S-substituted sulfenylthiocarbonate with a thiol that differs from the thiol used in the previous reaction.

14. The optical product as claimed in claim 12, wherein the component (B) thiol is 2,3-epithiopropylmercaptan, and the thiol used for synthesizing the component (A) is 1,2-dimercaptoethane, 1,2,3-trimercaptopropane, trimercaptomethane or dimercaptomethane.

15. The optical product as claimed in claim 12, wherein the component (B) thiol is 1,2-dimercaptoethane, 1,2,3-trimercaptopropane, trimercaptomethane or dimercaptomethane, and the thiol used for synthesizing the component (A) is vinylmercaptan, propargylmercaptan or 2,3-epithiopropylmercaptan.

16. An optical product comprising a polymer obtained through polymerization of the asymmetric disulfide compound of claim 1 with one or more compounds selected from episulfide compounds, epoxy compounds, mixtures of polythiols and polyisocyanates to form polythiourethanes, polythiols and homopolymerizable vinyl monomers.

17. The optical product as claimed in claim 16 which is a plastic lens.

18. An optical product comprising a polymer obtained through polymerization of the asymmetric disulfide compound of claim 2 with one or more compounds selected from episulfide compounds, epoxy compounds, mixtures of polythiols and polyisocyanates to form polythiourethanes, polythiols and homopolymerizable vinyl monomers.

19. The optical product as claimed in claim 18 which is a plastic lens.

20. An optical product comprising a polymer obtained through polymerization of the asymmetric disulfide compound of claim 3 with one or more compounds selected from episulfide compounds, epoxy compounds, mixtures of polythiols and polyisocyanates to form polythiourethanes, polythiols and homopolymerizable vinyl monomers.

21. The optical product as claimed in claim 20 which is a plastic lens.

22. An optical product comprising a polymer obtained through polymerization of the asymmetric disulfide compound of claim 4 with one or more compounds selected from episulfide compounds, epoxy compounds, mixtures of polythiols and polyisocyanates to form polythiourethanes, polythiols and homopolymerizable vinyl monomers.

23. The optical product as claimed in claim 22 which is a plastic lens.

24. An optical product comprising a polymer obtained through polymerization of the asymmetric disulfide compound of claim 5 with one or more compounds selected from episulfide compounds, epoxy compounds, mixtures of polythiols and polyisocyanates to form polythiourethanes, polythiols and homopolymerizable vinyl monomers.

25. The optical product as claimed in claim 24 which is a plastic lens.

* * * * *